United States Patent
Horng et al.

(10) Patent No.: US 10,413,210 B2
(45) Date of Patent: Sep. 17, 2019

(54) NON-CONTACT VITAL SIGN MONITORING SYSTEM

(71) Applicant: NATIONAL SUN YAT-SEN UNIVERSITY, Kaohsiung (TW)

(72) Inventors: Tzyy-Sheng Horng, Kaohsiung (TW); Mu-Cyun Tang, Kaohsiung (TW); Chao-Yun Kuo, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 369 days.

(21) Appl. No.: 15/391,968

(22) Filed: Dec. 28, 2016

(65) Prior Publication Data

US 2018/0078166 A1    Mar. 22, 2018

(30) Foreign Application Priority Data

Sep. 22, 2016    (TW) .............................. 105130608 A

(51) Int. Cl.
    *A61B 5/05*    (2006.01)
    *A61B 5/00*    (2006.01)
    (Continued)

(52) U.S. Cl.
    CPC .............. *A61B 5/05* (2013.01); *A61B 5/0002* (2013.01); *A61B 5/0205* (2013.01);
    (Continued)

(58) Field of Classification Search
    CPC ....... A61B 5/05; A61B 5/7278; A61B 5/0507; A61B 5/0205; A61B 5/0002;
    (Continued)

(56) References Cited

U.S. PATENT DOCUMENTS 8,721,554 B2    5/2014    Lin et al.
8,754,772 B2    6/2014    Horng et al.
(Continued)

FOREIGN PATENT DOCUMENTS

TW    201315437         4/2013
WO    2007/101343 A1    9/2007
(Continued)

OTHER PUBLICATIONS

Mu-Cyan Tang et al., A Self- and Mutually Injection-Locked Radar System for Monitoring Vital Signs in Real Time With Random Body Movement Cancellation, IEEE Transactions on Microwave Theory and Techniques, vol. 64, No. 12, Dec. 2016, Nov. 18, 2016, 4812-4822.
(Continued)

*Primary Examiner* — Rex R Holmes
(74) *Attorney, Agent, or Firm* — Jackson IPG PLLC; Demian K. Jackson

(57) ABSTRACT

A non-contact vital sign monitoring system transmits wireless signals to the same side of a biological subject via two antennas with different gains, and the two antennas receive two reflected signals from the biological subject with random body movement. Under a proper setup of the two antennas, the two reflected signals can be adjusted by an amplitude and phase adjusting unit to have the Doppler shift components caused by body movement with equal magnitude and out of phase and the Doppler shift components caused by vital signs with different magnitude. Therefore, the random body movement effect can be cancelled based on the relation between the two reflected signals in using the system to monitor the vital signs of the subject.

9 Claims, 5 Drawing Sheets

(51) Int. Cl.
*A61B 5/0205* (2006.01)
*G01S 7/03* (2006.01)
*G01S 7/35* (2006.01)
*G01S 7/40* (2006.01)
*G01S 13/536* (2006.01)
*G01S 13/87* (2006.01)
*G01S 13/88* (2006.01)
*A61B 5/024* (2006.01)
*A61B 5/08* (2006.01)
*G01S 13/34* (2006.01)

(52) U.S. Cl.
CPC .......... *A61B 5/0507* (2013.01); *A61B 5/7214* (2013.01); *A61B 5/7225* (2013.01); *A61B 5/7228* (2013.01); *A61B 5/7278* (2013.01); *G01S 7/034* (2013.01); *G01S 7/354* (2013.01); *G01S 7/40* (2013.01); *G01S 13/536* (2013.01); *G01S 13/87* (2013.01); *G01S 13/88* (2013.01); *A61B 5/024* (2013.01); *A61B 5/0816* (2013.01); *A61B 2562/0228* (2013.01); *A61B 2562/04* (2013.01); *G01S 13/34* (2013.01)

(58) Field of Classification Search
CPC ... A61B 5/7214; A61B 5/7228; A61B 5/7225; A61B 2562/0228; A61B 2562/04; A61B 5/024; A61B 5/0816; G01S 7/40; G01S 7/034; G01S 7/354; G01S 13/536; G01S 13/87; G01S 13/88; G01S 13/34
See application file for complete search history.

(56) References Cited

U.S. PATENT DOCUMENTS

| | | |
|---|---|---|
| 2010/0152600 A1 | 6/2010 | Droitcour et al. |
| 2010/0198083 A1 | 8/2010 | Lin et al. |
| 2012/0146796 A1 | 6/2012 | Margon et al. |
| 2012/0209087 A1* | 8/2012 | Horng ............... A61B 5/11 600/301 |
| 2015/0018676 A1 | 1/2015 | Barak |
| 2016/0154098 A1* | 6/2016 | Pu ..................... G01S 13/04 342/27 |

FOREIGN PATENT DOCUMENTS

| | | |
|---|---|---|
| WO | 2013/118121 A1 | 8/2013 |
| WO | 2014/159773 A1 | 10/2014 |
| WO | 2015/160272 A1 | 10/2015 |
| WO | 2015/174879 A1 | 11/2015 |

OTHER PUBLICATIONS

Jhao-Yun Guo, Study of Self- and Mutually Injection-Locked Radar for Vital Sign Detection with Random Body Movement Cancellation, Master Thesis of National Sun Yat-sen University, Sep. 2, 2016.

Mu-Cyun Tang et al., Same Side Dual SIL-Radar System for Real-Time Vital Sign Monitoring with Random Body Movement Cancellation, Microwave Symposium (IMS), 2016 IEEE MTT-S International, Date of Conference: May 22-27, 2016.

Taiwanese Office Action dated Mar. 1, 2017 for Taiwanese Patent Application No. 105130608, 3 pages.

European Search Report dated Dec. 1, 2017 for European Patent Application No. 17170926.4, 10 pages.

* cited by examiner

NON-CONTACT VITAL SIGN MONITORING SYSTEM

FIELD OF THE INVENTION

This invention generally relates to a non-contact vital sign monitoring system, and more particularly to a non-contact vital sign monitoring system able to cancel the random body movement effect.

BACKGROUND OF THE INVENTION

Vital sign monitoring system, extensively applied to healthcare and fitness equipment, can track health and exercise of a biological subject by capturing and analyzing the changes in vital signs.

In general, there are two types of conventional vital sign monitoring system, contact type and non-contact type. The contact type vital sign monitoring system has to contact the subject's skin for a long time for accurate detection of the subject's vital signs, and the subject's moving range may be limited by the wires connected to the contact type vital sign monitoring system, causing the subject to feel uncomfortable during monitoring. In contrast, the non-contact vital sign monitoring system transmits wireless signals to the subject, the subject's vital signs can be detected according to the Doppler shift of the reflected signals. However, the reflected signals caused by body movement of the subject will also cause Doppler shift to affect the vital sign monitoring. Therefore, how to cancel the random body movement effect is a key point for developing the non-contact vital sign monitoring system.

Please refer to U.S. Pat. No. 8,721,554, a prior art of non-contact vital sign monitoring system able to cancel the random body movement effect is described. The system configures two continuous-wave (CW) radar apparatus at opposite sides of the subject, and transmits wireless signals to the subject and receives reflected signals from the subject via the antennas, wherein the subject's body movement direction is opposite relative to the antennas of the two CW radar apparatus, but the subject's vital sign (e.g. respiration and heartbeat) movement direction is identical relative to the antennas of the two CW radar apparatus. For this reason, the system can use signal post-processing to cancel the random body movement effect on the detection of vital signs of the subject. However, the system is limited in configuration because the two CW radar apparatuses have to configure at opposite sides of the subject. The subject's vital signs are therefore difficult to detect by the system when the subject stands against a wall or lays on a bed.

Please refer to U.S. Pat. No. 8,754,772, a prior art of non-contact vital sign monitoring system is disclosed previously by the present inventors. Two self-injection locking (SIL) radar apparatuses configured at opposite sides of the subject transmit wireless signals to the subject using the same gain antennas. In the same principle, the subject's body movement direction is opposite relative to the antennas of the two SIL radar apparatus, and the subject's vital sign (e.g. respiration and heartbeat) movement direction is identical relative to the antennas of the two SIL radar apparatus. Hence, the two SIL radar apparatuses can be mutual-injection locked to each other to real-time cancel the random body movement effect on the detection of vital signs of the subject. However, the system is also limited in configuration because the two SIL radar apparatuses need to be placed at opposite sides of the subject.

SUMMARY

The primary object of the non-contact vital sign monitoring system of the present invention is to configure two radar devices at the same side of a biological subject to transmit wireless signals to the subject and receive the reflected signals from the subject via two different gain antennas for detecting Doppler shift in which the components due to body movement are approximately equal in magnitude and out of phase with each other, and the components due to vital signs are significantly different in magnitude. The Doppler shift components caused by body movement will be cancelled out when the two radar devices are in the self- and mutual-injection locking state, and the subject's vital signs can be detected because the Doppler shift components caused by vital signs will not be cancelled out.

The non-contact vital sign monitoring system of the present application comprises a first radar device for generating a first transmission signal, a first antenna for transmitting the first transmission signal to a side of a biological subject, wherein the first antenna has a first gain value, a second radar device for generating a second transmission signal and a second antenna for transmitting the second transmission signal to the same side of the subject, wherein the second antenna has a second gain value, and the first gain value is higher than the second gain value, wherein a first reflected signal and a second reflected signal are reflected from the subject after the first transmission signal and the second transmission signal are transmitted to the subject, the first reflected signal and the second reflected signal are both received by the first antenna and the second antenna and both delivered to the first radar device and the second radar device and, accordingly, the first radar device and the second radar device are operated in a self- and mutual-injection locking state.

The first and second antennas transmit the first and second transmission signals to the subject and receive the first and second reflected signals from the subject, respectively. When the first reflected signal is received by the first antenna and then delivered to the first radar device and the second reflected signal is received by the second antenna and then delivered to the second radar device, the two radar devices will enter the self-injection locking state to frequency modulate their output signals with the Doppler shifts of the two reflected signals, and moreover, the frequency modulations of the output signals of the two radar devices caused by the Doppler shift components due to body movement are adjusted to be equal in magnitude and out of phase. Meanwhile, the two radar devices will enter the mutual-injection locking state to output the signals having the same frequency modulation when the first reflected signal is received by the second antenna and then delivered to the second radar device and the second reflected signal is received by the first antenna and then delivered to the first radar device, wherein the frequency modulation of the output signals of the two radar devices is approximately the average of the frequency modulations of the output signals of two radar devices in the self-injection locking state. Because the frequency modulations of the output signals caused by the Doppler shift components due to body movement in the self-injection locking state are equal in magnitude and out of phase, they can be cancelled out in the mutual-injection locking state. However, because of the use of the two different gain antennas, the frequency modulations caused by the Doppler shift components due to vital signs have significantly different magnitude in the self-injection locking state and, therefore, they cannot be cancelled out in the mutual-injection locking state, so the vital signs of the subject can be obtained by frequency modulating one of the output signals of the two radar devices.

DETAILED DESCRIPTION OF THE INVENTION

Figure 1:
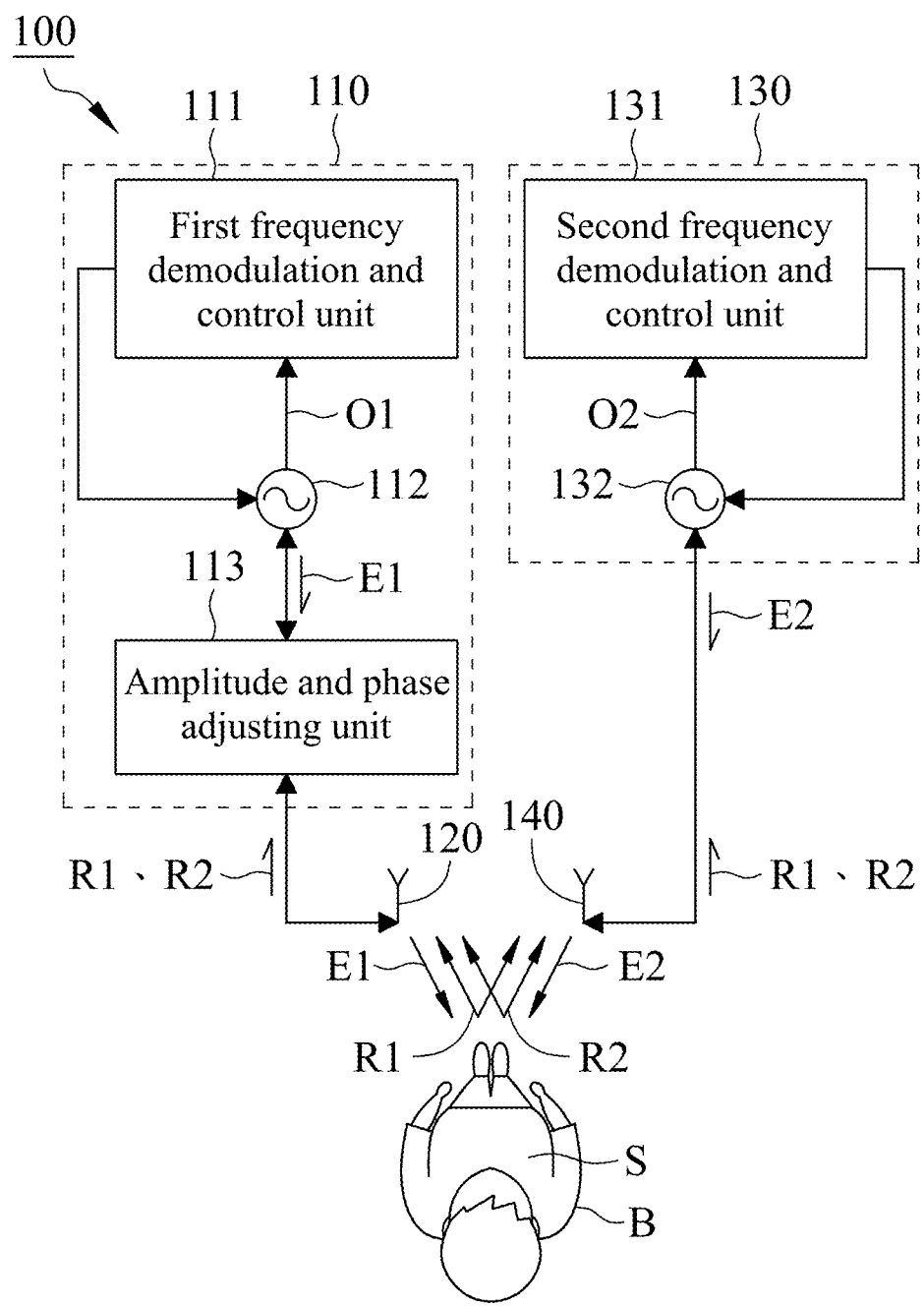
FIG. 1 is a schematic diagram illustrating a non-contact vital sign monitoring system in accordance with the first embodiment of the present invention.

With reference to FIG. 1, a non-contact vital sign monitoring system 100 in accordance with a first embodiment of the present invention comprises a first radar device 110, a first antenna 120, a second radar device 130 and a second antenna 140.

With reference to FIG. 1, the first radar device 110 includes a first frequency demodulation and control unit 111, a first voltage-controlled oscillator (VCO) 112 and an amplitude and phase adjusting unit 113, wherein the first VCO 112 is electrically connected with the first frequency demodulation and control unit 111 and the amplitude and phase adjusting unit 113. The first frequency demodulation and control unit 111 is used for controlling the frequency of a first transmission signal E1 generated from the first VCO 112 and demodulating an output signal O1 from the first VCO 112, wherein the first transmission signal E1 is delivered to the amplitude and phase adjusting unit 113, and the amplitude and phase adjusting unit 113 is used for adjusting the amplitude and phase of the first transmission signal E1.

The first antenna 120 is electrically connected to the amplitude and phase adjusting unit 113, wherein the first transmission signal E1 adjusted in amplitude and phase is delivered to the first antenna 120, and the first antenna 120 is used for transmitting the first transmission signal E1 toward a side S of a biological subject B. The first antenna 120 has a first gain value, and the first gain value is 12 dBi in this embodiment.

The second antenna 130 includes a second frequency demodulation and control unit 131 and a second voltage-controlled oscillator (VCO) 132 electrically connected to the second frequency demodulation and control unit 131. The second frequency demodulation and control unit 131 is used for controlling the frequency of a second transmission signal E2 generated from the second VCO 132 and demodulating an output signal O2 from the second VCO 132, wherein the first transmission signal E1 and the second transmission signal E2 are controlled to have similar frequency by the first frequency demodulation and control unit 111 and the second frequency demodulation and control unit 131, respectively, for ease of synchronizing the first VCO 112 and the second VCO 132 based on mutual injection locking.

The second antenna 140 is electrically connected to the second VCO 132, wherein the second transmission signal E2 is delivered to the second antenna 140, and the second antenna 140 is used for transmitting the second transmission signal E2 to a side S of the biological subject B, the first transmission signal E1 and the second transmission signal E2 are transmitted to the same side of the biological subject B. The second antenna 140 has a second gain value, wherein the first gain value is higher than the second gain value, and the second gain value is 6 dBi in this embodiment.

With reference to FIG. 1 again, the biological subject B respectively reflects a first reflected signal R1 and a second reflected signal R2 after the first transmission signal E1 and the second transmission signal E2 are transmitted to the biological subject B. The first antenna 120 and the second antenna 140 both receive the first reflected signal R1 and the second reflected signal R2, and the first reflected signal R1 and the second reflected signal R2 are delivered to the first radar device 110 and the second radar device 130 to make the first radar device 110 and the second radar device 130 operate in a self- and mutual-injection locking state.

The self-injection locking path of the first radar device 110: the first VCO 112→the amplitude and phase adjusting unit 113→the first antenna 120→the biological subject B→the first antenna 120→the amplitude and phase adjusting unit 113→the first VCO 112. The mutual-injection locking path of the first radar device 110: the second VCO 132→the second antenna 140→the biological subject B→the first antenna 120→the amplitude and phase adjusting unit 113→the first VCO 112. The self-injection locking path of the second radar device 130: the second VCO 132→the second antenna 140→the biological subject B→the second antenna 140→the second VCO 132. The mutual-injection locking path of the second radar device 130: the first VCO 112→the amplitude and phase adjusting unit 113→the first antenna 120→the biological subject B→the second antenna 140→the second VCO 132.

The first antenna 120 and the second antenna 140 in this embodiment transmit the first transmission signal E1 and the second transmission signal E2 to the biological subject B, respectively. The first antenna 120 receives the first reflected signal R1 from the biological subject B and delivers the first reflected signal R1 to the first VCO 112, and the second antenna 140 receives the second reflected signal R2 from the biological subject B and delivers the second reflected signal R2 to the second VCO 132, wherein the two VCOs 112 and 132 are in a self-injection locking state. The Doppler shifts of the reflected signals frequency modulate the output signals of the VCOs 112 and 132, and the frequency modulations of the output signals from the VCOs 112 and 132 caused by body movement are adjusted to be equal in magnitude and out of phase by the amplitude and phase adjusting unit 113. Besides, the VCOs 112 and 132 are in a mutual-injection locking state and both output signals having the same frequency modulation when the first reflected signal R1 is received by the second antenna 140 and then delivered to the second VCO 132 and the second reflected signal R2 is received by the first antenna 120 and then delivered to the first VCO 112, wherein the frequency modulations of the output signals from the VCOs 112 and 132 in the self- and mutual-injection locking state is about the average of the frequency modulations of the output signals from the VCOs 112 and 132 in the self-injection locking state only. Owing to the frequency modulations of the output signals caused by body movement are equal in magnitude and out of phase when the VCOs 112 and 132 are in the self-injection locking state only, they can be cancelled out in the self- and mutual-injection locking state. And owing to the frequency modulations of the output signals caused by vital signs from the VCOs 112 and 132 are significantly different due to the different gains of the antennas 120 and 140, they cannot be cancelled out in the self- and mutual-injection locking state. Therefore, the vital signs of the biological subject B can be obtained by frequency modulating one of the output signals O1 and O2 from the VCOs 112 and 132.

In addition, the antenna beams of the first antenna 120 and the second antenna 140 both are directed toward the same area on the side S of the biological subject B (e.g. sternum of human chest), but the gains of the first antenna 120 and the second antenna 140 are different. The Doppler shift components of the first reflected signal R1 and the second reflected signal R2 caused by body movement can be equal in magnitude and out of phase by adjusting the location and included angle of the first antenna 120 relative to the second antenna 140 and adjusting the amplitude and phase of the first reflected signal R1 by the amplitude and phase adjusting unit 113, so the Doppler shift components caused by body movement can be cancelled out when the first VCO 112 and the second VCO 132 are in the self- and mutual-injection locking state. And the Doppler shift components of the first reflected signal R1 and the second reflected signal R2 caused by vital signs are significantly different and cannot be cancelled out, so the vital signs can be preserved and monitored in real time.

Preferably, the first antenna 120 and the second antenna 140 are setup relative to the biological subject B in particular way to significantly enhance the difference between the Doppler shift components of the first reflected signal R1 and the second reflected signal R2 caused by vital signs for increasing the accuracy of vital sign monitoring.

Figure 2:
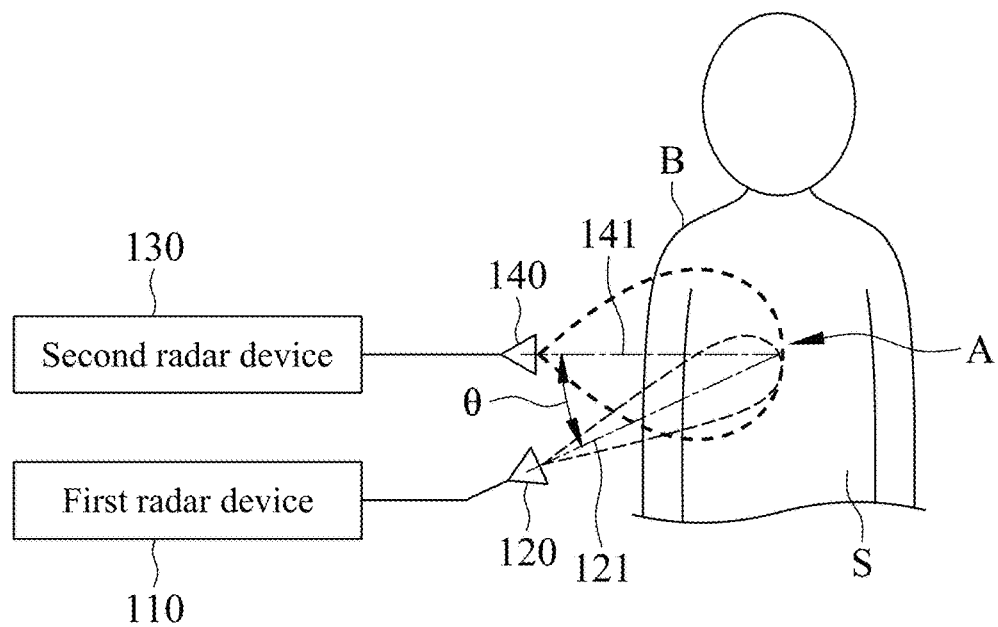
FIG. 2 is a schematic diagram illustrating an up-down antenna setup of a non-contact vital sign monitoring system in accordance with the second embodiment of the present invention.

With reference to FIG. 2, the first antenna 120 and the second antenna 140 in a second embodiment of the present invention are setup in an up-down configuration, wherein the first antenna 120 has a first central axis 121 and the second antenna 140 has a second central axis 141, and the first central axis 121 and the second central axis 141 both are directed to an area A on the side S of the biological subject B. The second central axis 141 is parallel to floor substantially, and the first central axis 121 is tilted relative to floor to form an included angle θ of less than 90 degrees between the first central axis 121 and the second central axis 141. In this embodiment, the included angle θ is 55 degrees when the system operates in the 2.4 GHz industrial, scientific and medical band.

Owing to the gain of the first antenna 120 is higher than that of the second antenna 140 in this embodiment, the magnitude of the first reflected signal R1 received by the first antenna 120 will be higher than that of the second reflected signal R2 received by the second antenna 140 when the first antenna 120 and the second antenna 140 are setup in parallel without tilt, so the Doppler component of the first reflected signal R1 caused by body movement will be larger than that of the second reflected signal R2 caused by body movement. Therefore, the first antenna 120 is tilted an angle θ with respect to the second antenna 140 to decrease the Doppler component of the first reflected signal R1 caused by body movement for getting close in magnitude to the Doppler component of the second reflected signal R2 caused by body movement. Moreover, the Doppler component of the first reflected signal R1 caused by vital signs is decreased more significantly because of the tilted angle θ of the first antenna 120, so it will be lower in magnitude than the Doppler component of the second reflected signal R2 caused by vital signs. The first radar device 110 and the second radar device 130 will operate in the self- and mutual-injection locking state to cancel out the Doppler shift components caused by body movement when the first reflected signal R1 and the second reflected signal R2 are delivered to the first radar device 110 and the second radar device 130, and the vital signs of the biological subject B can be preserved because the Doppler shift components caused by vital signs cannot be cancelled out.

Figure 3:
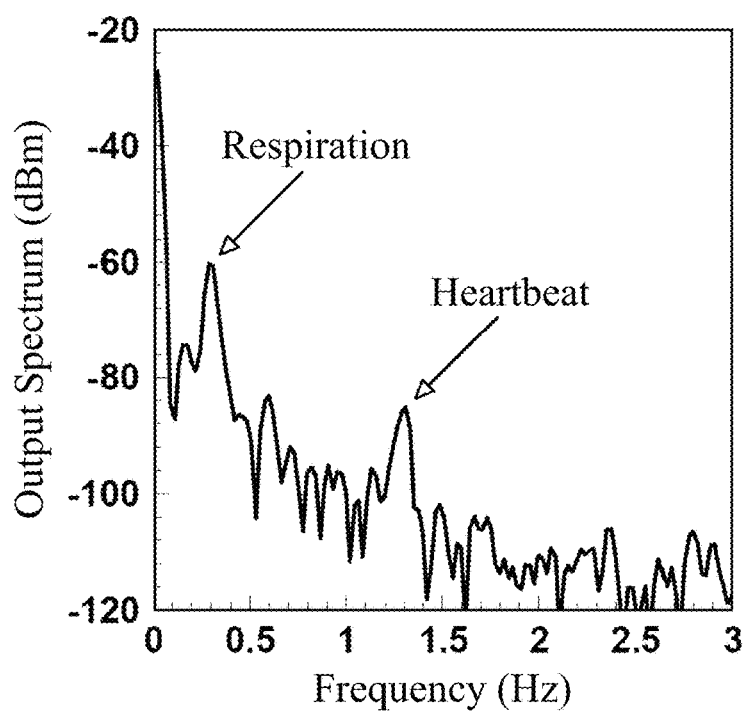
FIG. 3 is experimental results of monitoring a still subject using the non-contact vital sign monitoring system in accordance with the second embodiment of the present invention.
Figure 4:
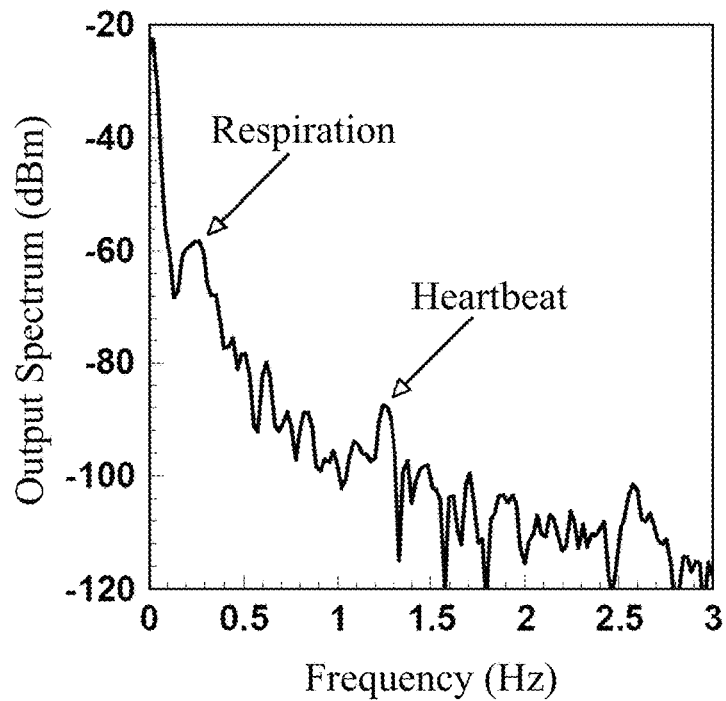
FIG. 4 is experimental results of monitoring a moving subject using the non-contact vital sign monitoring system in accordance with the second embodiment of the present invention.

With reference to FIG. 3 which shows experimental results of monitoring a human sitting still in front of the non-contact vital sign monitoring system 100 in accordance with the second embodiment at a distance of 70 cm, wherein the frequencies of respiration and heartbeat are clearly identified in FIG. 3, so it indicates that using the system of the second embodiment can detect the vital signs of the biological subject B accurately when the human body is still. With reference to FIG. 4 which shows experimental results of monitoring a human sitting in front of the non-contact vital sign monitoring system 100 at a distance of 70 cm in accordance with the second embodiment, and moving his upper body randomly within a target range from −3 to 3 cm, wherein the frequencies of respiration and heartbeat are also clearly identified in FIG. 4, so it indicates that using the system of the second embodiment can detect the vital signs of the biological subject B accurately when the human body is moving.

Figure 5:
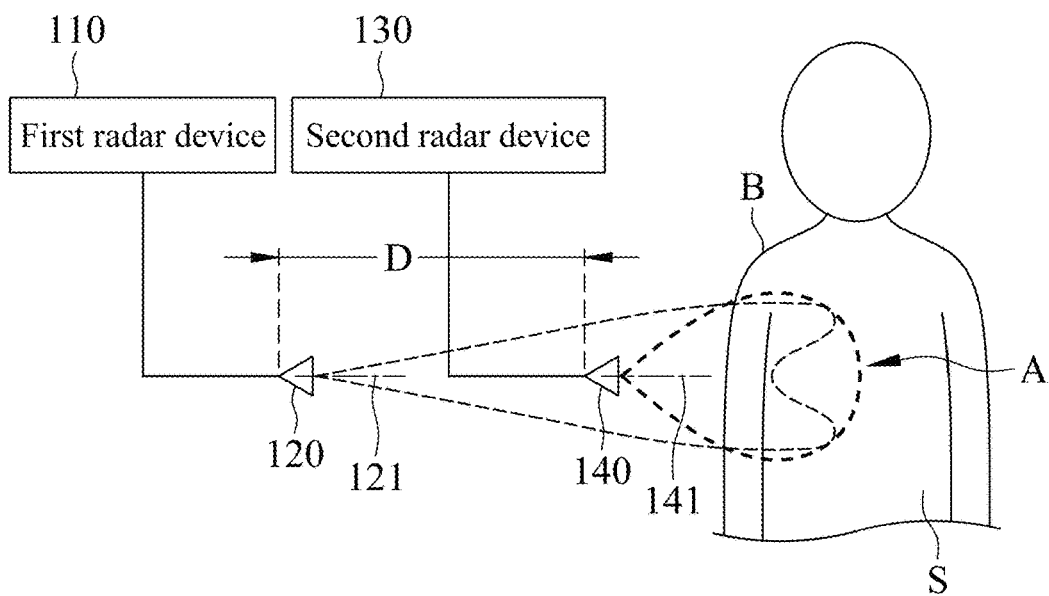
FIG. 5 is a schematic diagram illustrating a front-rear antenna setup of a non-contact vital sign monitoring system in accordance with the third embodiment of the present invention.

With reference to FIG. 5, the first antenna 120 and the second antenna 140 in a third embodiment of the present invention are setup in a front-rear configuration, wherein the first antenna 120 has a first central axis 121 and the second antenna 140 has a second central axis 141, and the first central axis 121 and the second central axis 141 both are directed to an area A on the side S of the biological subject B. There is a distance D between the first antenna 120 and the second antenna 140, and the second antenna 140 is located between the first antenna 120 and the biological subject B. In this embodiment, the distance D is 20 cm when the system operates in the 2.4 GHz industrial, scientific and medical band.

In the setup of the first antenna 120 and the second antenna 140 of the third embodiment, the first transmission signal E1 transmitted from the first antenna 120 is partially blocked by the metal plate of the second antenna 140 to decrease the Doppler component of the first reflected signal R1 caused by body movement for getting close in magnitude to the Doppler component of the second reflected signal R2 caused by body movement. Moreover, the Doppler component of the first reflected signal R1 caused by vital signs is decreased more significantly because of the blocking effect from the second antenna 140, so it will be lower in magnitude than the Doppler component of the second reflected signal R2 caused by vital signs. The first radar device 110 and the second radar device 130 will operate in the self- and mutual-injection locking state to cancel out the Doppler shift components caused by body movement when the first reflected signal R1 and the second reflected signal R2 are delivered to the first radar device 110 and the second radar device 130, and the vital signs of the biological subject B can be preserved because the Doppler shift components caused by vital signs cannot be cancelled out.

Figure 6:
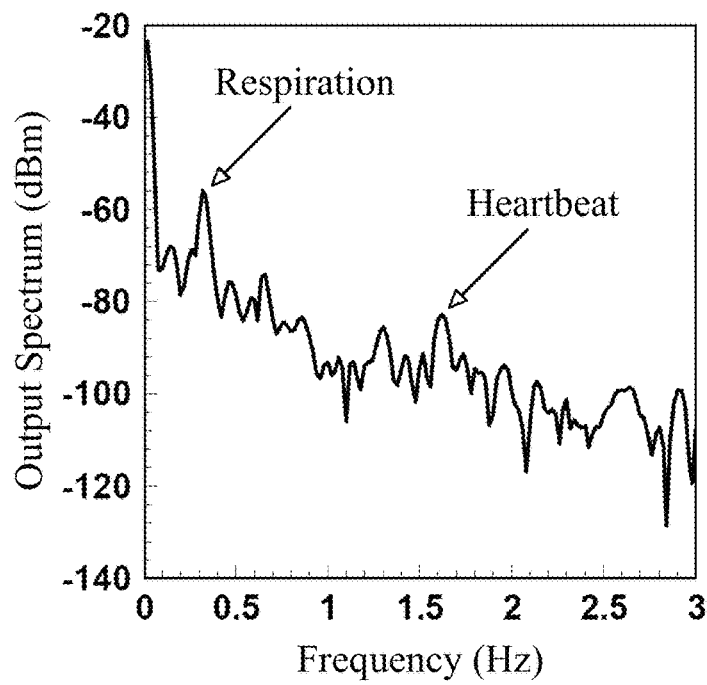
FIG. 6 is experimental results of monitoring a still subject using the non-contact vital sign monitoring system in accordance with the third embodiment of the present invention.
Figure 7:
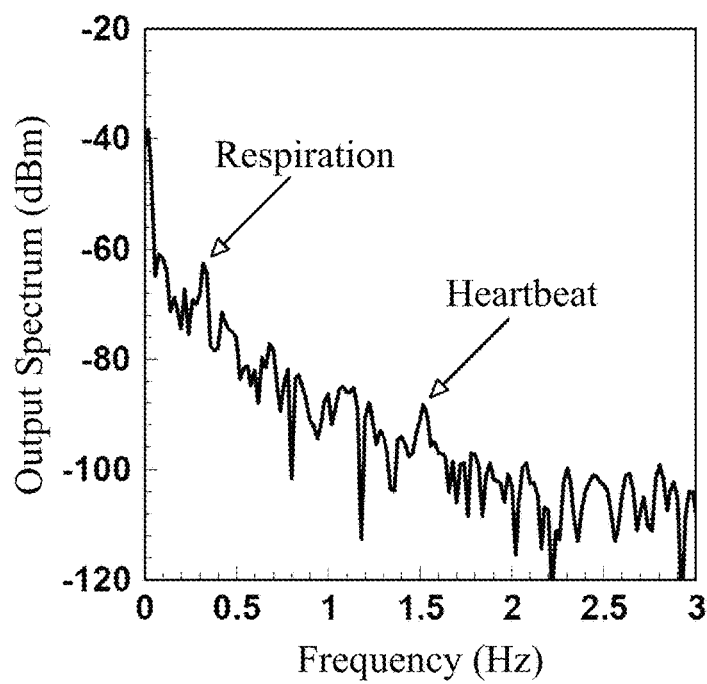
FIG. 7 is experimental results of monitoring a moving subject using the non-contact vital sign monitoring system in accordance with the third embodiment of the present invention.

With reference to FIG. 6 which shows experimental results of monitoring a human sitting still in front of the non-contact vital sign monitoring system 100 in accordance with the third embodiment at a distance of 70 cm, wherein the frequencies of respiration and heartbeat are clearly identified in FIG. 6, so it indicates that using the system of the third embodiment can detect the vital signs of the biological subject B accurately when the human body is still. With reference to FIG. 7 which shows experimental results of monitoring a human sitting in front of the non-contact vital sign monitoring system 100 at a distance of 70 cm in accordance with the third embodiment, and moving his upper body randomly within a target range from −3 to 3 cm, wherein the frequencies of respiration and heartbeat are also clearly identified in FIG. 7, so it indicates that using the system of the third embodiment can detect the vital signs of the biological subject B accurately when the human body is moving.

Figure 8:
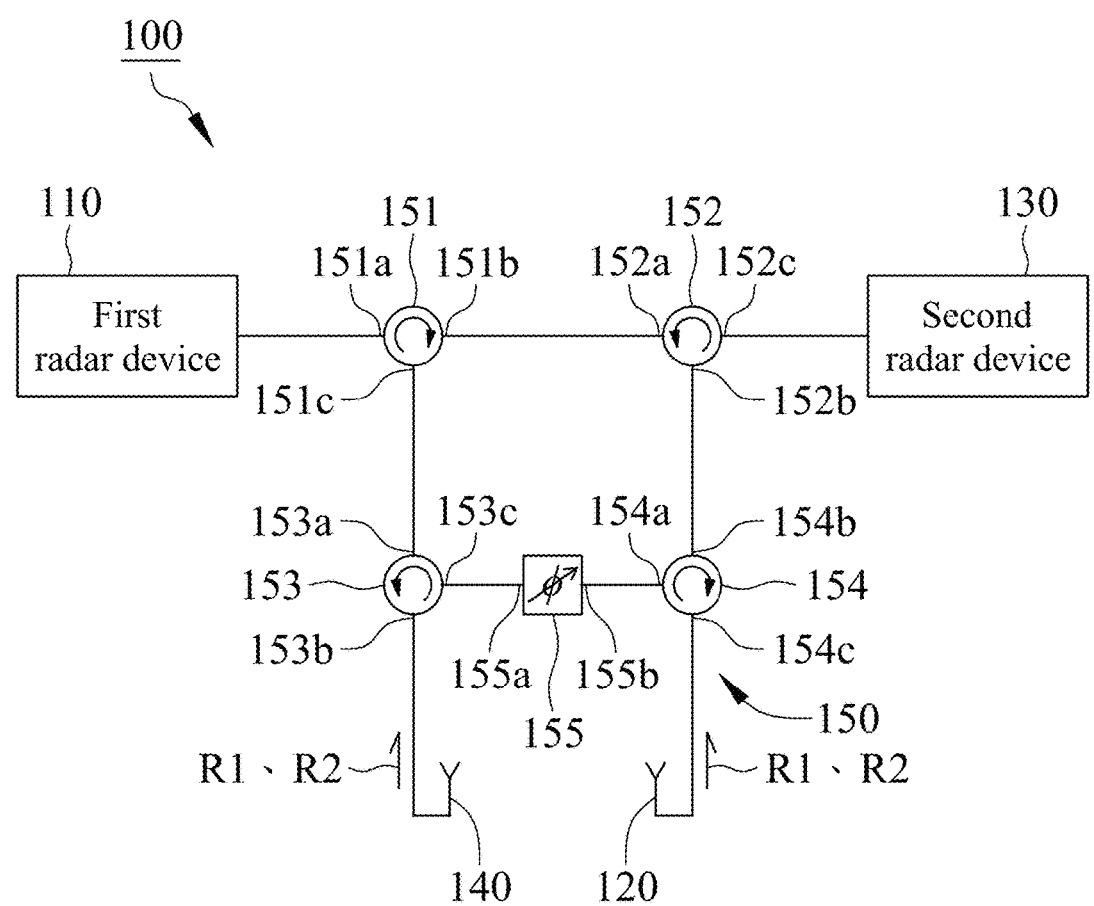
FIG. 8 is a schematic diagram illustrating a circulator array of a non-contact vital sign monitoring system in accordance with the fourth embodiment of the present invention.

With reference to FIG. 8, it is a schematic diagram showing the system of fourth embodiment. In the fourth embodiment, the first radar device 110 and the second radar device 130 are connected with each other using a circulator array 150 to operate in the self- and mutual-injection locking state with improved detection performance.

The circulator array 150 is electrically connected with the first radar device 110 and the second radar device 130, wherein the output signal from the first radar device 110 is delivered to the first antenna 120 via the circulator array 150, and the output signal from the second radar device 130 is delivered to the second antenna 140 via the circulator array 150.

With reference to FIG. 8, the circulator array 150 includes a first circulator 151, a second circulator 152, a third circulator 153, a fourth circulator 154 and a tunable phase shifter 155. The first circulator 151 is electrically connected with the first radar device 110, the second circulator 152 and the third circulator 153. The second circulator 152 is electrically connected with the second radar device 130 and the fourth circulator 154. The third circulator 153 is electrically connected with the tunable phase shifter 155 and the second antenna 140. The fourth circulator 154 is electrically connected with the tunable phase shifter 155 and the first antenna 120. The tunable phase shifter 155 is electrically connected with the third circulator 153 and the fourth circulator 154. In more detail, a first port 151a of the first circulator 151 is electrically connected to the first radar device 110, a second port 151b of the first circulator 151 is electrically connected to a first port 152a of the second circulator 152, and a third port 151c of the first circulator 151 is electrically connected to a first port 153a of the third circulator 153. A third port 152c of the second circulator 152 is electrically connected to the second radar device 130, and a second port 152b of the second circulator 152 is electrically connected to a second port 154b of the fourth circulator 154. A second port 153b of the third circulator 153 is electrically connected to the second antenna 140, and a third port 153c of the third circulator 153 is electrically connected to a first port 155a of the tunable phase shifter 155. A second port 155b of the tunable phase shifter 155 is electrically connected to a first port 154a of the fourth circulator 154, and a third port 154c of the fourth circulator 154 is electrically connected to the first antenna 120.

In this embodiment, the output signal from the first radar device 110 is input to the first port 151a of the first circulator 151 and output from the second port 151b, then input to the first port 152a of the second circulator 152 and output from the second port 152b, then input to the second port 154b of the fourth circulator 154 and output from the third port 154c, and then delivered to the first antenna 120 for transmission to the subject, wherein the first reflected signal R1 from the subject is received by the first antenna 120 and the second antenna 140. The first reflected signal R1 received by the first antenna 120 is input to the third port 154c of the fourth circulator 154 and output from the first port 154a, then input to the second port 155b of the tunable phase shifter 155 and output from the first port 155a, then input to the third port 153c of the third circulator 153 and output from the first port 153a, then input to third port 151c of the first circulator 151 and output from the first port 151a, and finally delivered to the first radar device 110, so the first radar device 110 is self-injection locked by the first reflected signal R1. The first reflected signal R1 received by the second antenna 140 is input to the second port 153b of the third circulator 153 and output from the third port 153c, then input to the first port 155a of the tunable phase shifter 155 and output from the second port 155b, then input to the first port 154a of the fourth circulator 154 and output from the second port 154b, then input to the second port 152b of the second circulator 152 and output from the third port 152c, and finally delivered to the second radar device 130, so the second radar device 130 is mutual-injection locked by the first reflected signal R1.

In contrast, the output signal from the second radar device 130 is input to the third port 152c of the second circulator 152 and output from the first port 152a, then input to the second port 151b of the first circulator 151 and output from the third port 151c, then input to the first port 153a of the third circulator 153 and output from the second port 153b, and then delivered to the second antenna 140 for transmission to the subject, wherein the second reflected signal R2 from the subject is received by the first antenna 120 and the second antenna 140. The second reflected signal R2 received by the second antenna 140 is input to the second port 153b of the third circulator 153 and output from the third port 153c, then input to the first port 155a of the tunable phase shifter 155 and output from the second port 155b, then input to the first port 154a of the fourth circulator 154 and output from the second port 154b, then input to the second port 152b of the second circulator 152 and output from the third port 152c, and finally delivered to the second radar device 130, so the second radar 130 is self-injection locked by the second reflected signal R2. The second reflected signal R2 received by the first antenna 120 is input to the third port 154c of the fourth circulator 154 and output from the first port 154a, then input to the second port 155b of the tunable phase shifter 155 and output from the first port 155a, then input to the third port 153c of the third circulator 153 and output from the first port 153a, then input to the third port 151c of the first circulator 151 and output from the first port 151a, and finally delivered to the first radar device 110, so the first radar device 110 is mutual-injection locked by the second reflected signal R2.

According to the aforementioned, the first radar device 110 and the second radar device 130 both can receive the first reflected signal R1 and the second reflected signal R2 via the circulator array 150 for operation in self- and mutual-injection locking state. The first reflected signal R1 and the second reflected signal R2 are both delivered to the first radar device 110 and the second radar device 130 through the tunable phase shifter 155, so adjusting the phase shift of the tunable phase shifter 155 can improve the detection performance of the first radar device 110 and the second radar device 130. The phase shift is adjusted between 0 and 90 degrees, wherein the adjusted phase shift is 13 degrees when the system is operated in the 2.4 GHz industrial, scientific and medical band.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A non-contact vital sign monitoring system comprising:
a first radar device for generating a first transmission signal;
a first antenna for transmitting the first transmission signal to a side of a subject, wherein the first antenna has a first gain value;
a second radar device for generating a second transmission signal; and
a second antenna for transmitting the second transmission signal to the same side of the subject, wherein the second antenna has a second gain value, and the first gain value is higher than the second gain value, wherein a first reflected signal and a second reflected signal are reflected from the subject after the first transmission signal and the second transmission signal are transmitted to the subject, the first reflected signal and the second reflected signal are both received by the first antenna and the second antenna and both delivered to the first radar device and the second radar device and, accordingly, the first radar device and the second radar device operate in a self- and mutual-injection locking state.

2. The non-contact vital sign monitoring system in accordance with claim 1, wherein the first radar device includes a first frequency demodulation and control unit and a first voltage-controlled oscillator (VCO), and the second radar device includes a second frequency demodulation and control unit and a second voltage-controlled oscillator (VCO), and wherein the first VCO is electrically connected to the first frequency demodulation and control unit for outputting the first transmission signal, and the second VCO is electrically connected to the second frequency demodulation and control unit for outputting the second transmission signal.

3. The non-contact vital sign monitoring system in accordance with claim 2, wherein the first radar further includes an amplitude and phase adjusting unit which is electrically connected with the first VCO and the first antenna, and wherein the amplitude and phase adjusting unit is used for adjusting amplitudes and phases of the first transmission signal and the first reflected signal.

4. The non-contact vital sign monitoring system in accordance with claim 1, wherein antenna beams of the first antenna and the second antenna are both directed toward a same area on the same side of the subject.

5. The non-contact vital sign monitoring system in accordance with claim 4, wherein the first antenna has a first central axis and the second antenna has a second central axis, and the first central axis and the second central axis are both directed to the same area on the same side of the subject, and wherein the second axis is parallel to a floor substantially and the first central axis is tilted relative to the floor to form an included angle of less than 90 degrees between the first central axis and the second central axis.

6. The non-contact vital sign monitoring system in accordance with claim 4, wherein the first antenna has a first central axis and the second antenna has a second central axis, and the first central axis and the second central axis are both directed to the same area on the same side of the subject, and wherein there is a distance between the first antenna and the second antenna, and the second antenna located between the first antenna and the subject blocks part of the antenna beam of the first antenna.

7. The non-contact vital sign monitoring system in accordance with claim 1 further comprises a circulator array electrically connected with the first radar device and the second radar device, wherein the first transmission signal from the first radar device is transmitted to the first antenna via the circulator array, and the second transmission signal from the second radar device is transmitted to the second antenna via the circulator array.

8. The non-contact vital sign monitoring system in accordance with claim 7, wherein the circulator array includes a first circulator, a second circulator, a third circulator, a fourth circulator and a tunable phase shifter, and wherein the first circulator is electrically connected with the first radar device, the second circulator and the third circulator, the second circulator is electrically connected with the second radar device and the fourth circulator, the third circulator is electrically connected with the tunable phase shifter and the second antenna, the fourth circulator is electrically connected with the tunable phase shifter and the first antenna, and the tunable phase shifter is electrically connected with the third circulator and the fourth circulator.

9. The non-contact vital sign monitoring system in accordance with claim 8, wherein a first port of the first circulator is electrically connected to the first radar device, a second port of the first circulator is electrically connected to a first port of the second circulator, a third port of the first circulator is electrically connected to a first port of the third circulator, a third port of the second circulator is electrically connected to the second radar device, a second port of the second circulator is electrically connected to a second port of the fourth circulator, a second port of the third circulator is electrically connected to the second antenna, a third port of the third circulator is electrically connected to a first port of the tunable phase shifter, a third port of the forth circulator is electrically connected to the first antenna, and a first port of the fourth circulator is electrically connected to a second port of the tunable phase shifter.

* * * * *